(12) United States Patent
Barmada

(10) Patent No.: US 8,109,939 B2
(45) Date of Patent: Feb. 7, 2012

(54) SYSTEM AND METHOD FOR REMOVING AN IMPLANTED CATHETER FROM A PATIENT

(75) Inventor: Hazem Barmada, Ocean Springs, MS (US)

(73) Assignee: Hazem Barmada, Ocean Springs, MS (US)

( * ) Notice: Subject to any disclaimer, the term of this patent is extended or adjusted under 35 U.S.C. 154(b) by 564 days.

(21) Appl. No.: 12/412,845

(22) Filed: Mar. 27, 2009

(65) Prior Publication Data

US 2010/0249799 A1    Sep. 30, 2010

(51) Int. Cl.
    *A61F 11/00* (2006.01)

(52) U.S. Cl. ....................................... 606/108; 606/190

(58) Field of Classification Search .............. 606/1, 108, 606/138, 148, 151, 153, 190; 600/201, 207; 128/898

See application file for complete search history.

(56) References Cited

U.S. PATENT DOCUMENTS

| 5,183,464 | A |   | 2/1993  | Dubrul et al.   |         |
|-----------|---|---|---------|-----------------|---------|
| 6,030,406 | A | * | 2/2000  | Davis et al.    | 606/190 |
| 6,117,150 | A | * | 9/2000  | Pingleton et al.| 606/190 |
| 6,197,016 | B1|   | 3/2001  | Fourkas et al.  |         |
| 6,468,289 | B1| * | 10/2002 | Bonutti         | 606/190 |
| 2002/0161395 | A1 | | 10/2002 | Douk et al.     |         |
| 2008/0161843 | A1 | | 7/2008  | Clague et al.   |         |

OTHER PUBLICATIONS

International Patent Application No. PCT/US2010/025839, Search Report and Written Opinion of the International Searching Authority dated Nov. 4, 2010, 11 pages.
Bard Access Systems, Brochure entitled: "Peritoneal Port Meeting the Demand of Intraperitoneal Chemotherapy," Found at: http://www.bardaccess.com/port-peritoneal.php.
Bard Access Systems, Patient Information entitled: "BardPort Implanted Ports," :Found at: http://www.bardaccess.com/port-peritoneal.php.
Angiodynamics Incorporated, Promotional Literature entitled, "Vascular Access Ports, Conventional Port Systems, Infuse-A-Port®," Found at: http://www.angiodynamics.com/pages/products/infuse_a_port.asp.
Angiodynamics Incorporated, Brochure entitled: "Ports Instructions For Use," Found at: http://www.angiodynamics.com/pages/products/infuse_a_port.asp.
Angiodynamics Incorporated, Brochure entitled: "Ports Patient Information," Found at: http://www.angiodynamics.com/pages/products/infuse_a_port.asp.

* cited by examiner

*Primary Examiner* — Kevin T Truong
(74) *Attorney, Agent, or Firm* — Conley Rose, P.C.

(57) ABSTRACT

A method comprising removing a port from a patient through an incision and coupling a rod disposed in a sheath to the end of a catheter. The method also includes sliding the sheath along the rod and catheter into tissue surrounding the catheter in a rotating manner to separate the tissue from the catheter until the catheter is able to freely be removed from the patient, and removing the catheter from the patient. The method may also include making a shorter second incision on the patient and exposing a portion of the catheter through the patient's skin to facilitate coupling of the rod with the catheter and retrieval of the catheter.

2 Claims, 4 Drawing Sheets

SYSTEM AND METHOD FOR REMOVING AN IMPLANTED CATHETER FROM A PATIENT

BACKGROUND

Numerous companies manufacture devices which enable medicines to be injected into a patient directly into the bloodstream and enable samples of blood to be taken from the patient. Other similar devices and catheters may be inserted for long-term dialysis or intravenous feeding. These devices are sometimes termed port-a-caths, infusa-ports, and venous access devices. Two manufacturers of these devices are C. R. Bard, Inc. and AngioDynamics. These devices often consist of a port, which also may be referred to as a drum, and a catheter which is coupled to the port. The catheter is typically inserted into a major vein, leading to a central vein, in the patient. Thus, the medicine is injected with a syringe, using a special needle, through the patient's skin directly into the port and carried directly into the patient's bloodstream through the catheter. Dialysis and feeding catheters are not usually coupled to a port, but come out through the skin. The section of the catheter outside the skin has a closure mechanism to keep the catheter shut and sterile when not in use. Just within the skin, a dialysis catheter has a Dacron cuff which anchors the catheter to the tissues and acts as a bacteriostatic bacterial barrier. All of these devices are usually intended to be implanted into the patient for long periods of time, e.g. months or even years. During this time, tissue may build up along the catheter and adhere to the catheter, both inside the vessel, along the tract, and outside the vessel, so that it may not be possible to remove the catheter without damaging the blood vessel causing serious, life-threatening bleeding. Accordingly, removing catheters that have been implanted for a long time may be problematic, and the present common practice, as advised by the manufacturer of these devices, is to leave the catheter in place indefinitely.

SUMMARY

The problems noted above are solved in large part by a system and method for removing an implanted port system and associated catheter from a patient. In some embodiments, the method comprises making a first incision on a patient, removing a port from the patient, and coupling a rod disposed in a sheath to a catheter. The method also includes sliding the sheath along the rod and catheter into tissue surrounding the catheter in a rotating manner to separate the tissue from the catheter until the catheter is able to freely be removed from the patient, and removing the catheter from the patient. In some embodiments, the method may also include making a second incision on the patient that is shorter than the first incision and closer to the blood vessel exposing a portion of the catheter through the patient's skin and delivering the distal portion of the catheter outside the skin. In the case of the dialysis catheter, the catheter is cut at the Dacron cuff then treated similarly.

Another illustrative embodiment includes a system for removing an implanted port system and associated catheter that comprises a rod containing a rod body and a rod handle. The rod handle is substantially straight. The system also comprises a hollow sheath containing a sheath body and a sheath handle. The sheath body is capable of bending to at least 90 degrees. The sheath body may not have a longitudinal rip apart seam embedded along its length and also may not have a valve. Both the rod handle and the sheath handle are made of a non-slip material. The hollow sheath's inner diameter may be approximately the diameter of a catheter that has been implanted into a patient.

Yet another illustrative embodiment includes a system for removing an implanted port system and associated catheter comprising means for coupling a rod to a catheter. The system also includes a means for separating tissue from the catheter so that the catheter is able to freely be removed from a patient.

BRIEF DESCRIPTION OF THE DRAWINGS

For a detailed description of various disclosed embodiments, reference will now be made to the accompanying drawings in which.

NOTATION AND NOMENCLATURE

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct mechanical connection. Thus, if a first device couples to a second device, that connection may be through a direct connection, or through an indirect connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to suggest that the scope of the disclosure, including the claims, is limited to that embodiment.

Figure 1:
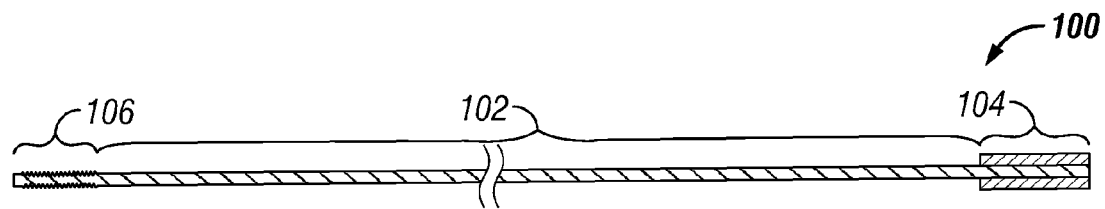
FIG. 1 shows a detailed view of a rod which may be used in removing a port-a-cath from a patient, in accordance with various embodiments of the invention.

FIG. 1 shows a detailed view of a rod 100 which may be used in removing a port-a-cath from a patient, in accordance with various embodiments of the invention. Rod 100 is comprised of rod body 102, rod handle 104, and threaded end 106. Rod body 102 is substantially straight. In at least some embodiments, "substantially straight" means straight plus or minus three degrees. Rod body 102 preferably is smooth, so that a sheath may slide along rod body 102 easily. Rod body 102 is approximately 2 millimeters in diameter, and approximately 19 centimeters in length, although it may be more or less in both diameter and length. Rod body 102 may be manufactured with a metal material; however, it may also be any material that remains rigid under tension.

Rod handle 104 may be 5 millimeters in diameter and two centimeters in length; however, other lengths and diameters may also be used. Rod handle 104 preferably is manufactured of a non-slip material. That is, rod handle 104 is manufactured with a material that will not slip in a physician's hand when rod handle 104 has body fluid (e.g. blood) on its surface. Some such materials include materials with a relatively high coefficient of friction compared to rod body 102's material, e.g. rubber, or a textured metal or plastic surface, e.g. ridged, knurled, or notched.

Threaded end 106 may have any diameter which allows it to be screwed into the end of a catheter. In some embodiments the diameter of threaded end 106 may be 1.35 millimeters. Preferably, the diameter of threaded end 106 is as small as possible so that the catheter does not bulge, but it should still be able to engage a catheter firmly and securely. Threaded end 106 may be 1 centimeter in length, although the length may vary.

Figure 2A:
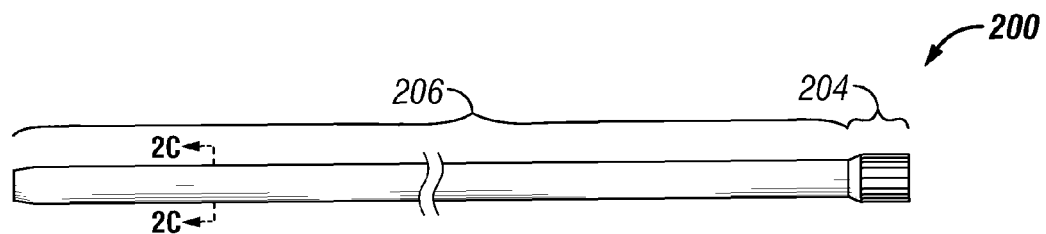
FIGS. 2a, 2b, and 2c show detailed views of a sheath which may be used in removing a port-a-cath from a patient, in accordance with various embodiments of the invention.
Figure 2B:
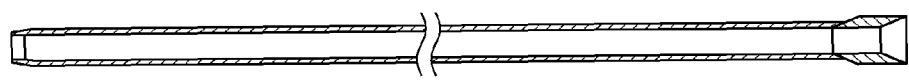
Figure 2C:

FIGS. 2a, 2b, and 2c show detailed views of a sheath 200 which may be used with rod 100 in removing a port-a-cath from a patient, in accordance with various embodiments of the invention. FIG. 2a shows a detailed view of sheath 200 as viewed as a whole, in accordance with various embodiments of the invention. Sheath 200 is comprised of sheath body 202 and sheath handle 204. Sheath body 202 may be fifteen centimeters in length, but may also be shorter or longer. Sheath body 202 is typically shorter than rod body 102 from FIG. 1. Sheath body 202 may be made of an opaque plastic material or a metal, e.g. coil wire, so that it is visible in x-rays and during fluoroscopy. Sheath body 202 also typically is bendable up to 90 degrees to enable sheath 200 to follow any bends in the catheter without damaging the catheter. While many prior art sheaths have longitudinal rip apart seams embedded along their lengths, in some embodiments sheath body 202 does not contain any longitudinal rip seams. In other embodiments, sheath body 202 does have rip seams. Additionally, many prior art sheaths have a stop valve near their ends. However, in some embodiments sheath 200 does not contain a stop valve. The outer diameter of sheath body 202 is usually 4 millimeters, 3.7 millimeters, or 3.3 millimeters, although other diameters would also allow sheath body 202 to implement an embodiment of the invention.

While the diameter of sheath handle 204 is typically larger than the diameter of sheath body 202, sheath handle 204 may be any diameter. Sheath handle 204 may be a flared out extension of sheath body 202. Typically, sheath handle 204 is 1 centimeter in length; however, other lengths may also be used. Sheath handle 204 is manufactured of a non-slip material. That is, sheath handle 204 is manufactured with a material that will not slip in a physician's hand when sheath handle 204 has body fluid (e.g. blood) on its surface. Some such materials include materials with a relatively high coefficient of friction compared to sheath body 204's material, e.g. rubber, or a textured metal or plastic surface, e.g. ridged, knurled, or notched.

FIGS. 2b and 2c show different cross sectional views of sheath 200, in accordance with various embodiments of the invention. FIG. 2b shows a cross sectional view along the entire length of sheath 200. FIG. 2c shows a cross sectional view of sheath 200 from its end. Sheath 200 is a hollow tube which narrows slightly at the tip. Thus, it has an inner diameter 206 at its tip as seen in FIG. 2c. Inner diameter 206 is typically equal to the diameter of a catheter that is intended to be removed, which may be 2.7 millimeters, 3 millimeters, or 3.3 millimeters, so that sheath 200 is capable of separating tissue from that catheter.

Figure 3:
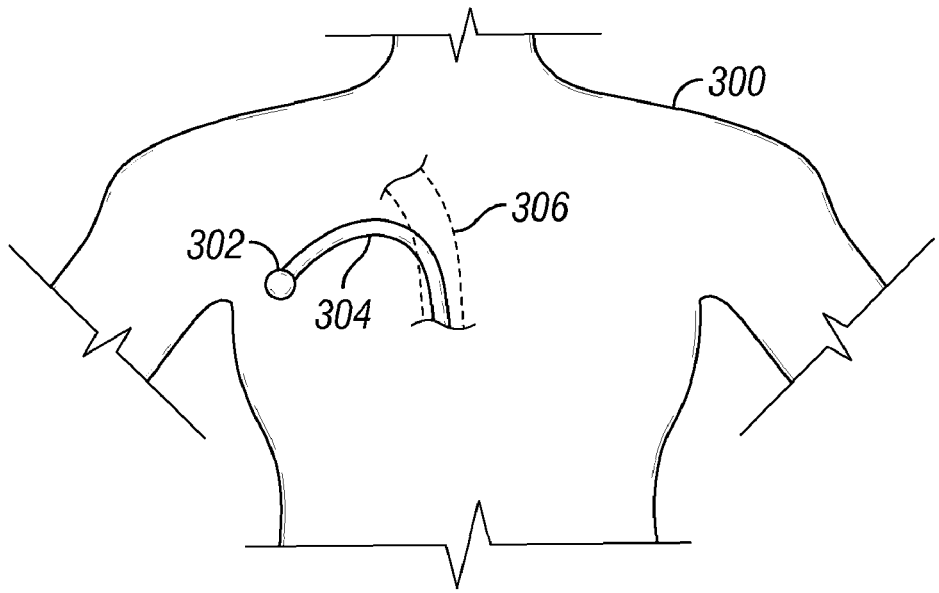
FIG. 3 shows a patient in whom a port and catheter have been implanted in accordance with various embodiments of the invention.

FIG. 3 shows a patient 300 in whom port 302 and catheter 304, collectively termed a port-a-cath, infusa-port, or venous access device, have been implanted in accordance with various embodiments of the invention. Catheter 304 is shown inserted into a blood vessel 306. Port 302, which also may be referred to as a drum, may be implanted in patient 300 just beneath the skin. Port 302 is typically implanted in the chest of patient 300 below the collarbone. However, port 302 may be implanted elsewhere beneath the skin of patient 300. Port 302 is usually 3 to 4 centimeters in diameter; however, it may be any size. Port 302 may include a septum, a self sealing rubber or plastic material, so that a special needle may be inserted through the septum into the cavity of port 302 to obtain blood samples or inject medicine directly into the bloodstream of patient 300 through catheter 304. Catheter 304 is a flexible tube that couples to port 302 and blood vessel 306. Thus, medicine that is injected into port 302 flows directly into blood vessel 306 and thence, the bloodstream of patient 300.

Port 302 and catheter 304 are intended to be implanted into patient 300 for long periods of time (i.e. weeks, months, or years). During this time, tissue may build up along and adhere to catheter 304, both inside blood vessel 306 and outside blood vessel 306, so that it is not possible to safely move catheter 304 without tearing the blood vessel 306, causing catastrophic bleeding.

Figure 4:
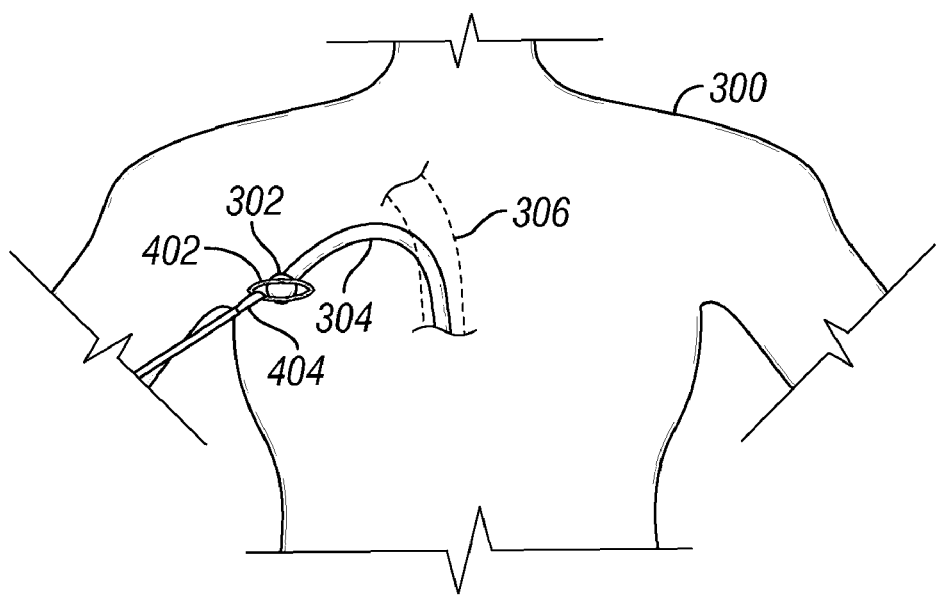
FIG. 4 shows a patient on whom an incision is made to remove a port, in accordance with various embodiments of the invention.
Figure 5:
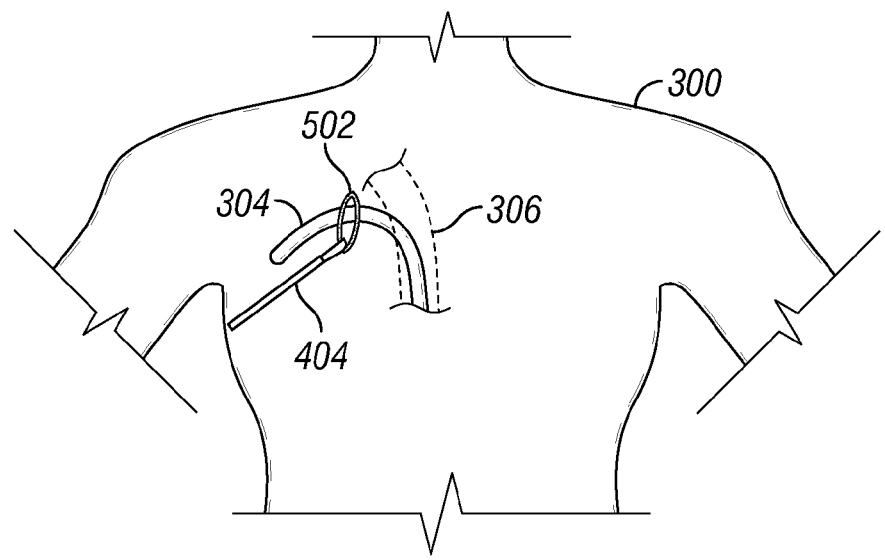
FIG. 5 shows a patient in which a port has been removed but a catheter remains implanted, in accordance with various embodiments of the invention.
Figure 6:
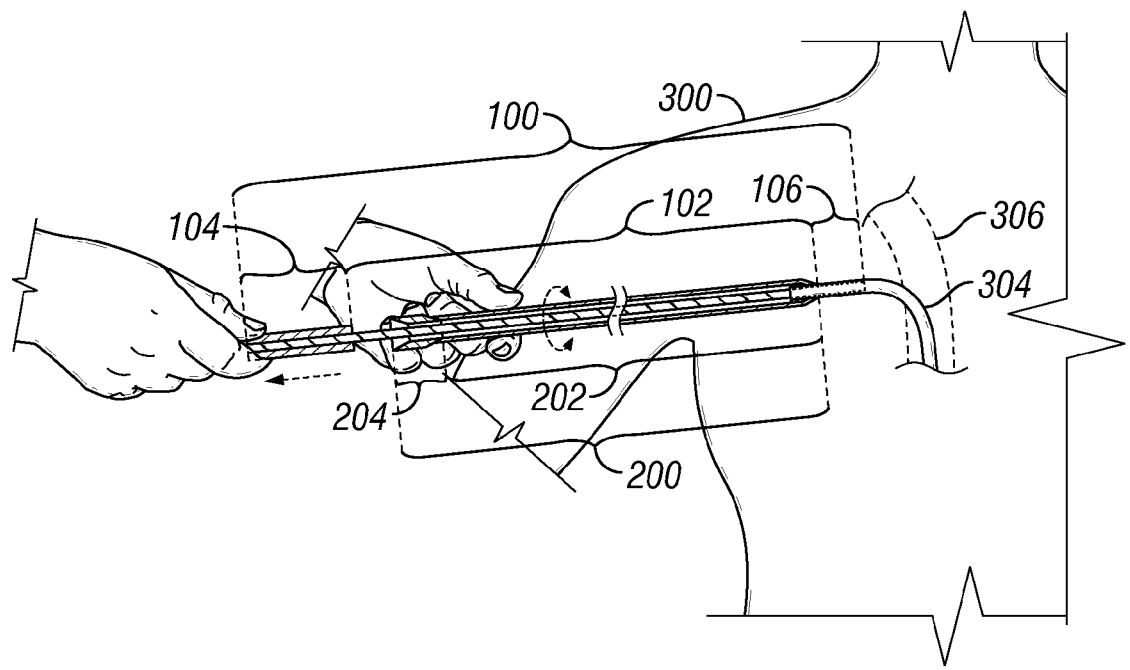
FIG. 6 shows a sheath and a rod for removing a catheter from a patient, in accordance with various embodiments of the invention.

FIGS. 4-6 illustrate an exemplary technique for safely removing catheter 304 from patient 300. FIG. 4 shows patient 300 on whom an incision 402 is made to remove port 302. Incision 402 is made on patient 300 directly above or adjacent to port 302 using a scalpel 404. Incision 402 is usually the same length as is the diameter of port 302, 3 to 4 centimeters; however, the length may be any length that would allow port 302 to be removed from patient 300. Port 302 is decoupled (e.g. cut or pulled off) from catheter 304 and removed from patient 300 through incision 402.

In FIG. 5 the port 302 has been removed but the catheter 304 remains implanted in patient 300. Preferably another incision 502 is made on patient 300 using scalpel 304 as close to the point that catheter 304 enters blood vessel 306 as possible; however, incision 502 may be made in any location that would allow a length of catheter 304 to be brought outside patient 300 for easier handling by the physician making the incision. Incision 502 may be shorter in length than incision 402 from FIG. 4, and usually is made to be as short as possible, yet large enough to be able to remove catheter 304 from patient 300. In some embodiments, incision 502 is 0.5 to 1 centimeter in length.

The end of catheter 304 that was decoupled from port 302 is then pulled out through incision 502, so that a section of catheter 304 is protruding from the body of patient 300. Preferably, at least 2.5 centimeters protrudes from the body of patient 300; however, a shorter section of catheter 304 may also protrude from the body of patient 300 as well.

FIG. 6 shows sheath 200 and a rod 100 from FIGS. 1 and 2 for removing catheter 304 from patient 300, in accordance with various embodiments of the invention. As discussed previously, rod 100 is a solid cylindrical shaped device comprising rod body 102, rod handle 104, and threaded end 106. Sheath 200 comprises sheath body 202 and a sheath handle 204, both of which are hollow tubes in continuity. Rod 100 is inserted through sheath 200 and then coupled (e.g. screwed) with the end of catheter 304 which is protruding from the body of patient 300. If after screwing rod 100 into the end of catheter 304, the end bulges too large to be pulled into sheath 200, rod 100 may be coupled to catheter 304 within sheath 200 by inserting a portion of catheter 304 into sheath 200 and then screwing rod 100 into catheter 304 within sheath 200. As mentioned previously, during the time catheter 304 has been implanted in patient 300, tissue builds up surrounding catheter 304 making it difficult to remove from patient 300. Sheath 200 is slid along rod 100 and catheter 304 in a rotating motion to separate the tissue from catheter 304. At all times, catheter 304 is preferably held taught by maintaining gentle traction on rod 100. Once all of the tissue is separated from catheter 304, so that catheter 304 may move freely, catheter 304 is removed from patient 300.

Figure 7:
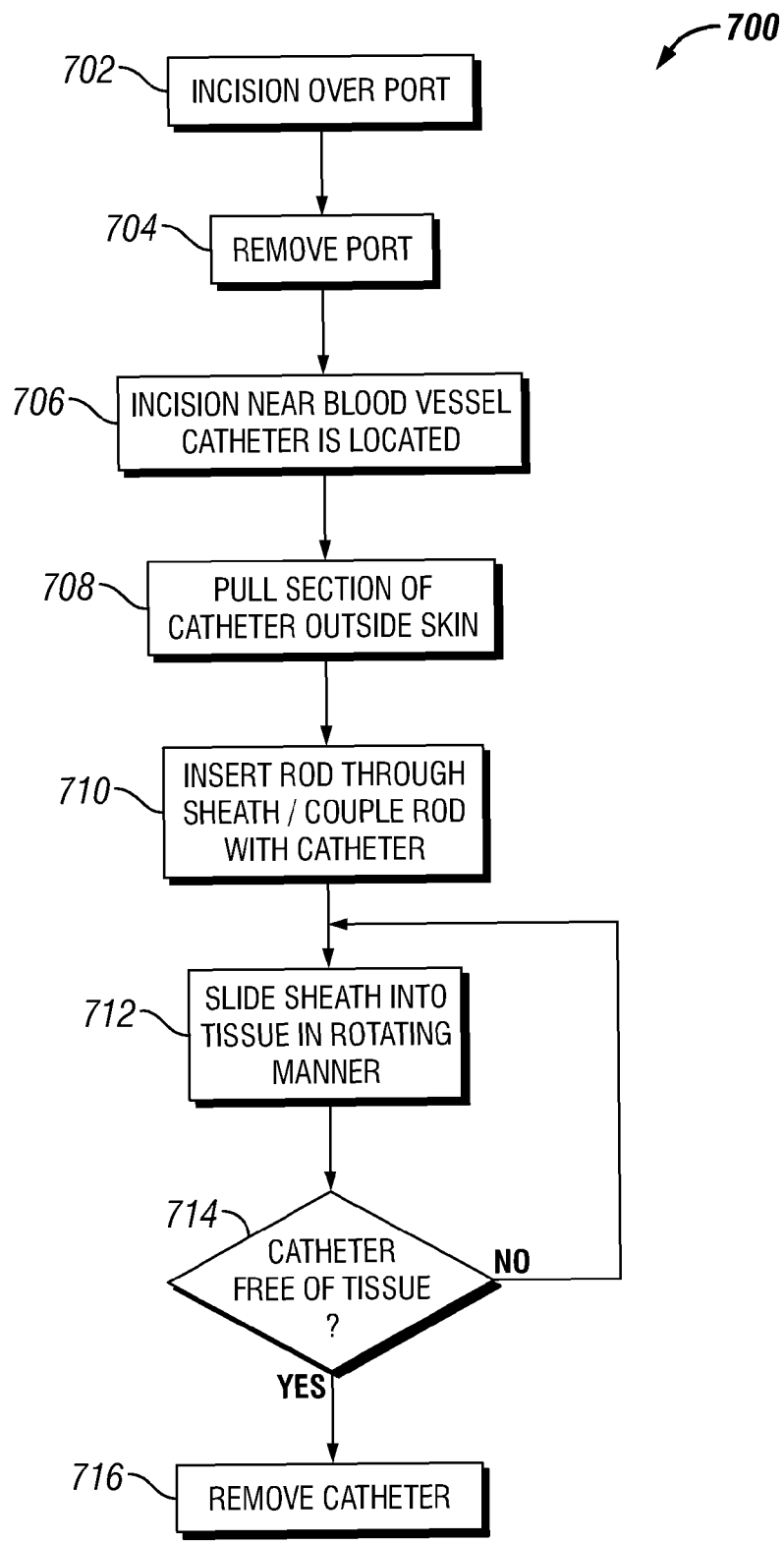
FIG. 7 shows an illustrative flow diagram of a method implemented in accordance with embodiments of the invention.

FIG. 7 shows an illustrative flow diagram of a method 700 implemented in accordance with various embodiments of the invention. Method 700 comprises, in block 702, making an incision above port 302 from FIG. 4. This incision preferably is large enough to enable the removal of port 302. The method continues in block 704 with the removal of port 302. In block 706, another incision is made near blood vessel 306 in which catheter 304, both from FIG. 5, is located. This second incision is preferably much smaller than the first incision and need only be large enough to allow the distal part of catheter 304 to be pulled through. Method 700 continues, in block 708, with an end section of catheter 304 being pulled through the second incision, so that typically this end section protrudes at least 2.5 centimeters from the patient's body.

Method 700 also comprises, in block 710, inserting rod 100 through a hollow sheath 200, both from FIGS. 1-2, and coupled to the end of catheter 304 which is protruding from the patient's body. Rod 100 is typically coupled with catheter 304 by screwing a threaded end of rod 100 into catheter 304. In block 712, sheath 200 is slid along rod 100 and catheter 304, which is maintained taught, in a rotating motion to separate any adherent, built-up tissue from catheter 304.

The method continues, in block 714, with a determination of whether catheter 304 is free of all surrounding tissue. If catheter 304 is capable of freely being withdrawn from the patient's body, then it is free of the surrounding tissue, otherwise, it is not free. If catheter 304 is not free of the surrounding tissue, then the method continues in block 712 with the sliding of sheath 200 along catheter 304 in a rotating manner to separate tissue from catheter 304. If however, catheter 304 is free of all surrounding tissue, catheter 304 is removed from the patient's body, as illustrated in block 716.

Prior to method 700 it would be prudent to obtain an X-ray film or use fluoroscopy to locate the course of the catheter and position of the tip of the catheter to be removed. Fluoroscopy should also be used to follow the sheath as it advances over the catheter, especially as the sheath approaches the tip of the catheter.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method for removing an implanted port and associated catheter comprising:
    making a first incision on a patient;
    removing the port from the patient;
    coupling a rod disposed in a sheath to the catheter;
    sliding the sheath along the rod and catheter into tissue surrounding the catheter in a rotating manner to separate the tissue from the catheter until the catheter is able to freely be removed from the patient; and
    removing the catheter from the patient.

2. The method of claim 1, further comprising:
    making a second incision on the patient that is shorter in length than the first incision; and
    exposing a portion of the catheter through the patient's skin.

* * * * *